US012453660B2

(12) United States Patent
Arai et al.

(10) Patent No.: US 12,453,660 B2
(45) Date of Patent: Oct. 28, 2025

(54) CONNECTING SHEET AND GARMENT STICKING ARTICLE

(71) Applicant: 3M INNOVATIVE PROPERTIES COMPANY, St. Paul, MN (US)

(72) Inventors: Nobuharu Arai, Sagamihara (JP); Marina Kawazoe, Sagamihara (JP)

(73) Assignee: 3M Innovative Properties Company, St. Paul, MN (US)

( * ) Notice: Subject to any disclaimer, the term of this patent is extended or adjusted under 35 U.S.C. 154(b) by 596 days.

(21) Appl. No.: 17/595,392

(22) PCT Filed: May 26, 2020

(86) PCT No.: PCT/IB2020/054981
§ 371 (c)(1),
(2) Date: Nov. 16, 2021

(87) PCT Pub. No.: WO2020/240415
PCT Pub. Date: Dec. 3, 2020

(65) Prior Publication Data
US 2022/0313504 A1 Oct. 6, 2022

(30) Foreign Application Priority Data
May 31, 2019 (JP) ................................ 2019-102321

(51) Int. Cl.
*A61F 13/551* (2006.01)
*A61F 13/56* (2006.01)
*A61F 13/62* (2006.01)

(52) U.S. Cl.
CPC .... *A61F 13/55135* (2013.01); *A61F 13/5611* (2013.01); *A61F 13/622* (2013.01)

(58) Field of Classification Search
CPC ............ A61F 13/55135; A61F 13/5611; A61F 13/622; A44B 18/0061; A44B 18/0065;
(Continued)

(56) References Cited

U.S. PATENT DOCUMENTS 4,946,527 A * 8/1990 Battrell ................. A61F 13/581 24/444
4,959,265 A 9/1990 Wood
(Continued)

FOREIGN PATENT DOCUMENTS

CN 106176060 A 12/2016
JP 2001040330 2/2001
(Continued)

OTHER PUBLICATIONS

JP_2006296974_A (Year: 2006).*
International Search Report for PCT International Application No. PCT/IB2020/054484, mailed on Jul. 14, 2020, 4 pages.

*Primary Examiner* — Catharine L Anderson
*Assistant Examiner* — Hans Kaliher
(74) *Attorney, Agent, or Firm* — Katherine M. Scholz; Colene H. Blank

(57) ABSTRACT

To provide a connecting sheet that can reduce noise generated when peeled from an object. A connecting sheet is a connecting sheet stacked on the object to be connected to the object, and includes: a sheet substrate having a first main surface and a second main surface; a first adhesive layer formed on the first main surface of the sheet substrate; and a plurality of hook components that protrude from the first main surface of the sheet substrate in a first direction and are spaced at intervals in a second direction in which the first main surface extends, and the hook components each includes: a column portion that extends from the sheet substrate in the first direction and protrudes from a surface of the first adhesive layer, and a head portion that extends from a tip of the column portion in the second direction, and the lower surface of the head portion is covered with the adhesive material.

5 Claims, 9 Drawing Sheets

(58) Field of Classification Search
CPC ............ A44B 18/0015; A44B 18/0019; A44B 18/0042; Y10T 428/24017; B29L 2031/729
See application file for complete search history.

(56) References Cited

U.S. PATENT DOCUMENTS

| | | | | | |
|---|---|---|---|---|---|
| 5,525,663 | A | | 6/1996 | Oien | |
| 5,672,404 | A | * | 9/1997 | Callahan, Jr. ...... | A44B 18/0073 604/389 |
| 5,786,062 | A | | 7/1998 | Callahan, Jr. et al. | |
| 5,933,927 | A | | 8/1999 | Miller et al. | |
| 9,541,291 | B2 | | 1/2017 | Wolff | |
| 2009/0294729 | A1 | | 12/2009 | Harada | |
| 2014/0268625 | A1 | | 9/2014 | Sherrer | |
| 2019/0008705 | A1 | | 1/2019 | Katoh | |

FOREIGN PATENT DOCUMENTS

| | | | | | |
|---|---|---|---|---|---|
| JP | 2006296974 | A | * | 11/2006 | |
| JP | 2010115563 | | | 5/2010 | |
| JP | 5893759 | | | 3/2016 | |
| JP | 2017057258 | | | 3/2017 | |
| JP | 2017167035 | | | 9/2017 | |
| JP | 2017179061 | | | 10/2017 | |
| WO | WO 2017-179474 | | | 10/2017 | |
| WO | WO-2019043640 | A1 | * | 3/2019 | ........... A61F 13/565 |

* cited by examiner

| | Comparative Example 1 | Example 1 | Comparative Example 2 |
|---|---|---|---|
| Configuration | Hook Components (No Adhesive Layer) | Hook Component + Adhesive Layer | Adhesive Layer (No Hook Component) |
| Hook Component Height (μm) | 250 | 250 | No Hook Component |
| Adhesive Material Configuration | No Adhesive Material | Quintac3620: Quintone M100/4:6 | |
| Frequency (Hz) | Application Amount (gsm) | 40 | 40 |
| 31.5 | 15.5 | 16.4 | 28.5 |
| 63 | 16.9 | 18.6 | 32.8 |
| 125 | 19 | 20.6 | 36.4 |
| 250 | 34.2 | 30.3 | 47.1 |
| 500 | 45.1 | 40.2 | 55.5 |
| 1000 | 50 | 48.8 | 59.2 |
| 2000 | 57.4 | 56 | 65.3 |
| 4000 | 60.2 | 58.1 | 67.2 |
| 8000 | 58 | 61.9 | 66.1 |
| Adhesive Strength of SUS Adhesive Material Only | 0 | 12.9 | 12.9 |
| Cotton Shear Force | 31.6 | 35.8 | 37.8 |

*FIG. 6*

| | Comparative Example 1 | Example 2 | Comparative Example 3 |
|---|---|---|---|
| Configuration | Hook Components (No Adhesive Layer) | Hook Component + Adhesive Layer | Adhesive Layer (No Hook Component) |
| Hook Component Height (µm) | 250 | 250 | No Hook Component |
| Adhesive Material Configuration | No Adhesive Material | Quintac3620:Quintone M100/6:4 | |
| Frequency (Hz) | Application Amount (gsm) | 60 | 60 |
| 31.5 | 15.5 | 16.7 | 17.7 |
| 63 | 16.9 | 16.8 | 17.9 |
| 125 | 19 | 20 | 19.7 |
| 250 | 34.2 | 24.5 | 31.7 |
| 500 | 45.1 | 28.7 | 42.3 |
| 1000 | 50 | 39.1 | 48.3 |
| 2000 | 57.4 | 43.4 | 54 |
| 4000 | 60.2 | 52.3 | 58 |
| 8000 | 58 | 58.2 | 58 |
| Adhesive Strength of SUS Adhesive Material Only | 0 | 5.3 | 5.3 |
| Cotton Shear Force | 31.6 | 91.6 | 18.5 |

*FIG. 7*

| | Comparative Example 1 | Example 3 | Comparative Example 4 |
|---|---|---|---|
| Configuration | Hook Components (No Adhesive Layer) | Hook Component + Adhesive Layer | Adhesive Layer (No Hook Component) |
| Hook Component Height (μm) | 250 | 250 | No Hook Component |
| Adhesive Material Configuration | No Adhesive Material | Quintac3270:Quintone M100/5:5 | |
| Frequency (Hz) | Application Amount (gsm) | 60 | 60 |
| 31.5 | 15.5 | 17.7 | 22.5 |
| 63 | 16.9 | 18.1 | 29.7 |
| 125 | 19 | 24.1 | 38.5 |
| 250 | 34.2 | 34.5 | 41.8 |
| 500 | 45.1 | 37.5 | 52.2 |
| 1000 | 50 | 44.2 | 56.3 |
| 2000 | 57.4 | 55.6 | 61.3 |
| 4000 | 60.2 | 57.1 | 65.1 |
| 8000 | 58 | 58.4 | 63.9 |
| Adhesive Strength of SUS Adhesive Material Only | 0 | 15.3 | 15.3 |
| Cotton Shear Force | 31.6 | 119.6 | 118.5 |

*FIG. 8*

| | | Example 1 | Example 2 | Example 3 | Example 4 | Example 5 | Comparative Example 5 |
|---|---|---|---|---|---|---|---|
| Configuration | | Hook Component + Adhesive Layer | Hook Component + Adhesive Layer | Hook Component + Adhesive Layer | Hook Component + Adhesive Layer | Hook Component + Adhesive Layer | Adhesive Layer (No Hook Component) |
| Hook Component Height (µm) | | 250 | 250 | 250 | 80 | 430 | No Hook |
| Adhesive Material Configuration | | Quintac3620: Quintone M100/4:6 | Quintac3620: Quintone M100/6:4 | Quintac3270: Quintone M100/5:5 | Kraton D1107:Quintone M100:A25 30/53/17 | Quintac3270 :Quin toneM100/5:5 | Hot melt |
| Frequency (Hz) | Application Amount (gsm) | 40 | 60 | 60 | 12 | 70 | 30 |
| 31.5 | | 16.4 | 16.7 | 17.7 | 15.7 | 20 | 20.6 |
| 63 | | 18.6 | 16.8 | 18.1 | 17.7 | 20 | 24.3 |
| 125 | | 20.6 | 20 | 24.1 | 21.4 | 24.1 | 33.8 |
| 250 | | 30.3 | 24.5 | 34.5 | 29.9 | 44.1 | 45.4 |
| 500 | | 40.2 | 28.7 | 37.5 | 42.5 | 57.5 | 51.4 |
| 1000 | | 48.8 | 39.1 | 44.2 | 50.2 | 65.2 | 59.5 |
| 2000 | | 56 | 43.4 | 55.6 | 57.3 | 65.1 | 62.3 |
| 4000 | | 58.1 | 52.3 | 57.1 | 61.6 | 69.1 | 64.8 |
| 8000 | | 61.9 | 58.2 | 58.4 | 60.2 | 66.4 | 65.1 |
| Adhesive Strength of SUS Adhesive Material Only | | 12.9 | 5.3 | 15.3 | 9.6 | 15.3 | 2.2 |
| Cotton Shear Force | | 35.8 | 91.6 | 119.6 | 17.2 | | 31.6 |

*FIG. 9*

CONNECTING SHEET AND GARMENT STICKING ARTICLE

CROSS REFERENCE TO RELATED APPLICATIONS

This application is a national stage filing under 35 U.S.C. 371 of PCT/IB2020/054981, filed May 26, 2020, which claims the benefit of Japanese Application No. 2019-102321, filed May 31, 2019, the disclosure of which is incorporated by reference in its/their entirety herein.

TECHNICAL FIELD

One form of the present invention relates to a connecting sheet and a garment sticking article.

BACKGROUND

Conventionally, to fix an article to a garment or the like, a connecting sheet using an adhesive material is used. An absorbent article such as a napkin is fixed to garments such as underwear via the adhesive material of the connecting sheet. For example, JP2010-115563A describes a connecting sheet having a slip-prevention adhesive layer for releasably attaching an article to garments. The connecting sheet has an adhesive layer on a main surface of a sheet substrate.

When the article such as the napkin is peeled from the garment, the adhesive layer of the connecting sheet is peeled from the garment. In this case, noise is generated as the adhesive layer is peeled from the garment. A conventional connecting sheet has a problem in that the noise at peeling from the garment is large. Therefore, there has been a demand for reducing noise generated when peeling the connecting sheet from an object such as the garment.

SUMMARY

A connecting sheet from one aspect of the present invention is a connecting sheet stacked on the object to be connected to the object, and includes: a sheet substrate having a first main surface and a second main surface; a first adhesive layer formed on the first main surface of the sheet substrate; and a plurality of hook components that protrude in a first direction from the first main surface of the sheet substrate and are spaced at intervals in a second direction in which the first main surface extends, and the hook components each includes: a column portion that extends from the sheet substrate in the first direction and protrudes from a surface of the first adhesive layer, and a head portion that extends from a tip of the column portion in the second direction, and at least a lower surface of the head portion is covered with an adhesive material.

According to the present invention, noise generated when peeling the connecting sheet from the object may be reduced.

BRIEF DESCRIPTION OF THE DRAWINGS

FIG. 6 is a table illustrating experimental results of Example and Comparative Examples.

FIG. 7 is a table illustrating experimental results of Example and Comparative Examples.

FIG. 8 is a table illustrating experimental results of Example and Comparative Examples.

FIG. 9 is a table illustrating experimental results of Examples and Comparative example.

DETAILED DESCRIPTION

Figure 1:
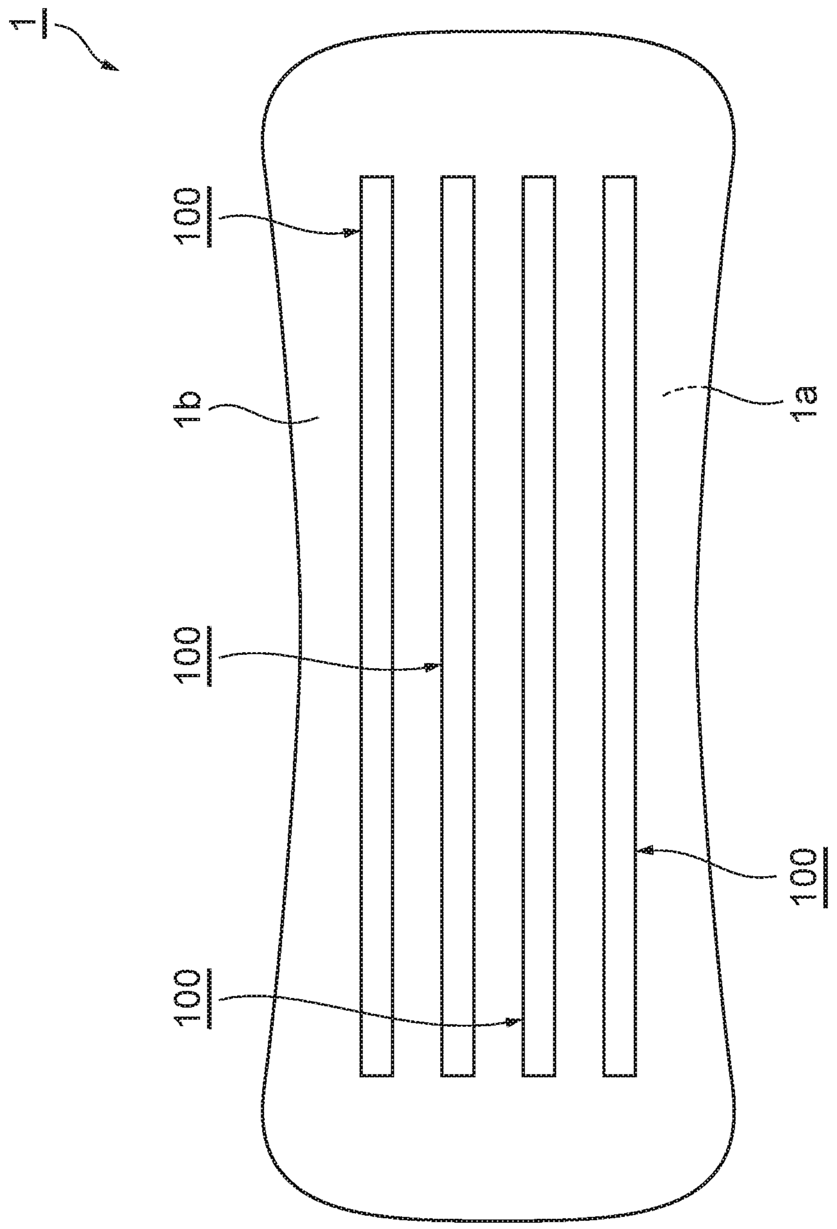
FIG. 1 is a view illustrating a napkin including a connecting sheet in accordance with an embodiment.

In the following, various embodiments will be described in detail with reference to drawings. Note that the same reference signs are used for the same or corresponding portions in the drawings.

FIG. 1 is a view illustrating a napkin including a connecting sheet according to an embodiment of the present invention. A napkin 1 includes a front surface 1*a* that faces the skin and has liquid permeability, a back surface 1*b* (connecting surface) that faces a garment and has liquid impermeability, and connecting sheets 100 provided on the back surface 1*b*. The back surface 1*b* is a connecting surface connected to the garment. In the example illustrated in FIG. 1, the connecting sheets 100 are provided in the plurality of regions of the back surface 1*b* at intervals. Note that the number of regions where the connecting sheets 100 are provided, the shape of each region, and the dimension of each region are not limited thereto, and can be arbitrarily designed. In addition, the article to which the connecting sheets 100 are applied is not limited to the napkin, and may be applied to, for example, a light incontinence pad, a pocket warmer (stuck to garments), or the like. The napkins and light incontinence pads may be collectively referred to as absorbent articles. The absorbent articles are also referred to as garment sticking articles including a pocket warmer or the like stuck to garments.

Figure 2:
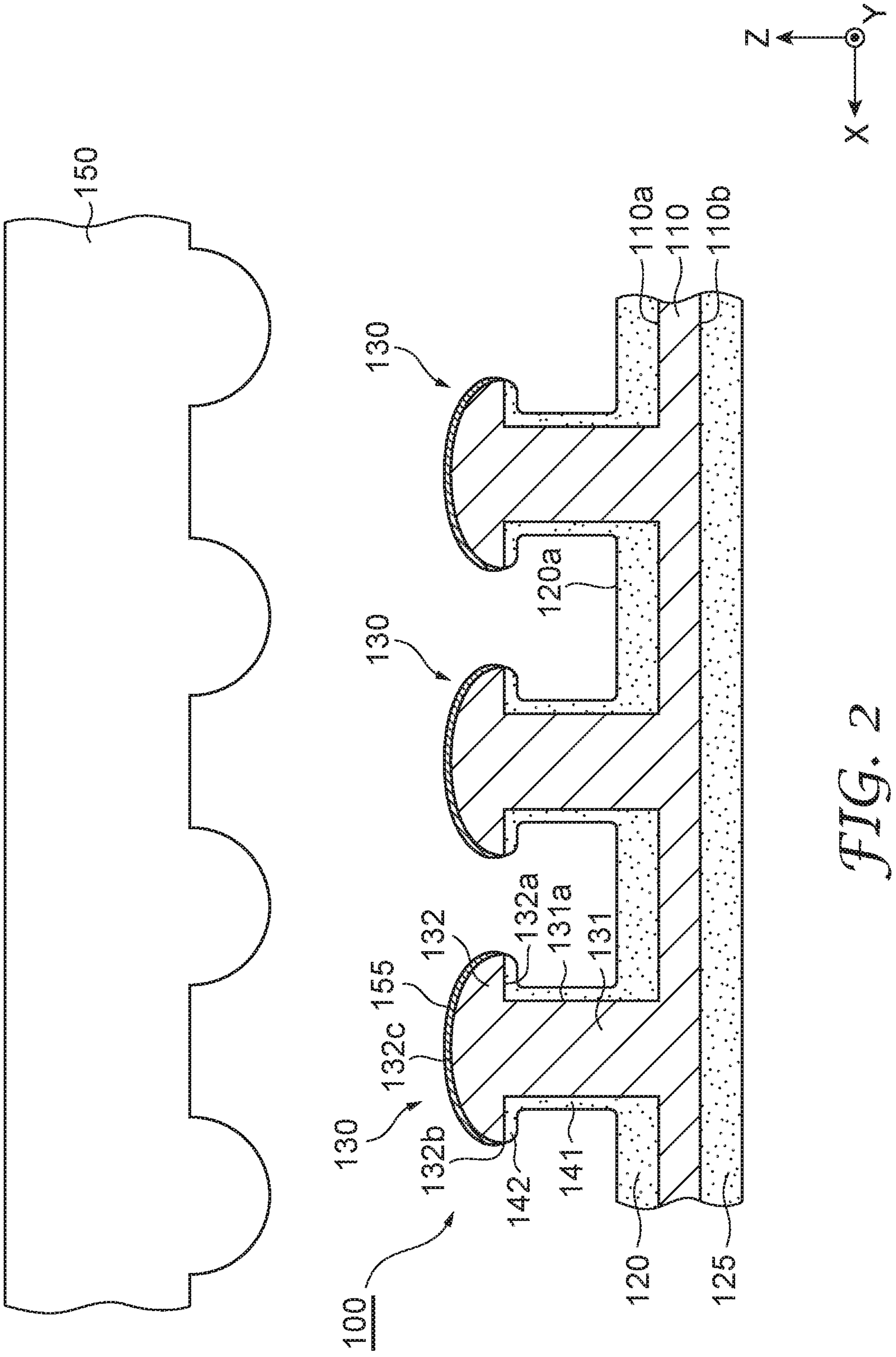
FIG. 2 is a cross sectional view illustrating a part of the connecting sheet in accordance with the embodiment.

Next, a configuration of the connecting sheet 100 will be described with reference to FIG. 2. FIG. 2 is a cross sectional view illustrating a part of the connecting sheet 100 in accordance with an embodiment. For the purpose of explanation, FIG. 2 also illustrates the XYZ Cartesian coordinate system.

The connecting sheet 100 is stacked on an object 150 such as underwear and connected thereto. As a result, the connecting sheet 100 can fix the napkin 1 to the object 150 such as garments. As illustrated in FIG. 2, the connecting sheets 100 each include a sheet substrate 110, a first adhesive layer 120, a second adhesive layer 125, and a plurality of hook components 130. In the present embodiment, a direction that is orthogonal to the sheet substrate 110 is defined as a Z-axis direction (first direction). A direction that is orthogonal to the Z-axis direction is defined as an X-axis direction, and a direction that is orthogonal to the Z-axis direction and the X-axis direction is defined as a Y-axis direction.

The sheet substrate 110 has a substantially sheet-like shape and has a first main surface 110*a* and a second main surface 110*b* that are opposed to each other in the Z-axis direction. The sheet substrate 110 extends in an XY-plane direction (second direction). In other words, the first main surface 110*a* and the second main surface 110*b* extend in the XY-plane direction. The plurality of hook components 130 is formed on the first main surface 110*a*. The sheet substrate 110 is formed from resin materials, for example, poly (ethylene terephthalate), polyamide such as nylon, poly (styrene-acrylonitrile), poly (acrylonitrile-butadiene-styrene), polyolefin such as polypropylene, plasticized vinyl chloride, and polyester. The thickness of the sheet substrate 110 is approximately 20 μm to 100 μm.

The first adhesive layer 120 is formed on the first main surface 110*a* of the sheet substrate 110. The first adhesive layer 120 is provided so as to fill spaces between the plurality of hook components 130. The first adhesive layer 120 is formed so as to cover the substantially entire surface of the first main surface 110*a* (except for the positions of the hook components 130). Examples of the material for the first adhesive layer 120 include natural rubber/resin copolymers, synthetic rubber/resin copolymers, and acrylate copolymers. The thickness of the first adhesive layer 120 may be 10 μm or more, or 20 μm or more, and may be 100 μm or less, or 90 μm or less. The applied amount may be 10 gsm or more, or 20 gsm or more, and may be 100 gsm or less, or 90 gsm or less. The adhesive strength of the first adhesive layer 120 may be 2 (N/25 mm) or more, or 4 (N/25 mm) or more, and may be 14 (N/25 mm) or less, or 8 (N/25 mm) or less. The adhesive strength of the first adhesive layer 120 is a value defined by the method JISZ 0237.

The second adhesive layer 125 is formed on the second main surface 110*b* of the sheet substrate 110. The material for the second adhesive layer 125 is the same adhesive material as the material for the first adhesive layer 120. The first adhesive layer 120 and the second adhesive layer 125 may be formed from the same adhesive material or may be formed from different adhesive materials. The second adhesive layer 125 may be omitted. The thickness of the first adhesive layer 120 may be 10 μm or more, or 20 μm or more, and may be 120 μm or less, or 110 μm or less.

The hook components 130 protrude from the first main surface 110*a* of the sheet substrate 110 in the Z-axis direction (first direction). The hook components 130 are spaced at intervals in the XY-plane direction in which the first main surface 110*a* extends. The hook components may be arranged in a grid pattern that is perpendicular to the XY-plane direction, and may be arranged in a grid pattern that is oblique from the XY-plane direction, a staggered pattern, a random pattern, and the like. Examples of the material of the hook components 130 include poly (ethylene terephthalate), polyamide such as nylon, poly (styrene-acrylonitrile), poly (acrylonitrile-butadiene-styrene), polyolefin such as polypropylene, plasticized vinyl chloride, and polyester. Note that the hook components 130 may be formed from the same material as the material for the sheet substrate 110 and integrally formed with the sheet substrate 110. Alternatively, the hook components 130 may be configured as a separate member formed from a material that is different from the material for the sheet substrate 110. In addition, the density in which the hook components 130 are arranged may be, for example, approximately 500 to 5000 per square inch or approximately 1600 to 3500 per square inch.

The average height of the hook component 130 from the first main surface 110*a* may be 170 μm or more, or may be 90 μm or more. The average height of the hook component 130 from the first main surface 110*a* may be 330 μm or less, or may be 310 μm or less.

The hook components 130 protrude from the surface 120*a* on the Z-axis positive side of the first adhesive layer 120 in the Z-axis direction. The difference between the average height of the hook components 130 (the height measured from the first main surface 110*a* of the sheet substrate 110) and the average thickness of the first adhesive layer 120 (the thickness measured from the first main surface 110*a* of the sheet substrate 110), that is, the protruding amount of the hook components 130 from the first adhesive layer 120 may be 10 μm or more, or 100 μm or more. The protruding amount may be 600 μm or less, or may be 500 μm or less. Note that the protruding amount is ultimately determined within the scope of the subject matter of the present invention according to various factors such as the size and density of the hook components 130, the material and thickness of the adhesive material, and the type of the object. In addition, the height of all of the hook components 130 in the connecting sheet 100 may be uniform (variations in the range of manufacturing errors are allowed), or may be different in different regions.

The hook components 130 each include a column portion 131 and a head portion 132. The column portion 131 is a portion that extends from the sheet substrate 110 in the Z-axis direction and protrudes from the surface 120*a* of the first adhesive layer 120. The head portion 132 is a portion that extends from a tip of the column portion 131 in the XY-plane direction. Note that the shape of the column portions 131 and the head portions 132 of all of the hook components 130 in the connecting sheet 100 may be the same (variations in the range of manufacturing errors are allowable), or may be different in different regions.

The hook component 130 includes adhesive material applied portions 141, 142 formed by covering a portion protruding from the first adhesive layer 120 with an adhesive material. Specifically, an outer circumferential surface 131*a* of the column portion 131 is covered with the adhesive material. As a result, the adhesive material applied portion 141 is formed on the outer circumference of the column portion 131. Further, a lower surface 132*a* of the head portion 132 is covered with the adhesive material. As a result, the adhesive material applied portion 142 is formed on the lower side of the head portion 132. The thickness of the adhesive material applied portion 141 is not particularly limited, but may be 5 μm or more, or may be 10 μm or more. The thickness may be 50 μm or less, or may be 40 μm or less. The thickness of the adhesive material applied portion 142 is not particularly limited, but may be 5 μm or more, or may be 10 μm or more. The thickness may be 100 μm or less, or may be 80 μm or less.

The adhesive material applied portion 142 is formed across the entire region between an inner circumferential end (a connection portion of the column portion 131 and the head portion 132) and an outer circumferential end 132*b* on the lower surface 132*a* of the head portion 132. Accordingly, the adhesive material applied portion 142 of the head portion 132 further extends to the outer circumferential side than the adhesive material applied portion 141 of the column portion 131.

Figure 3A:
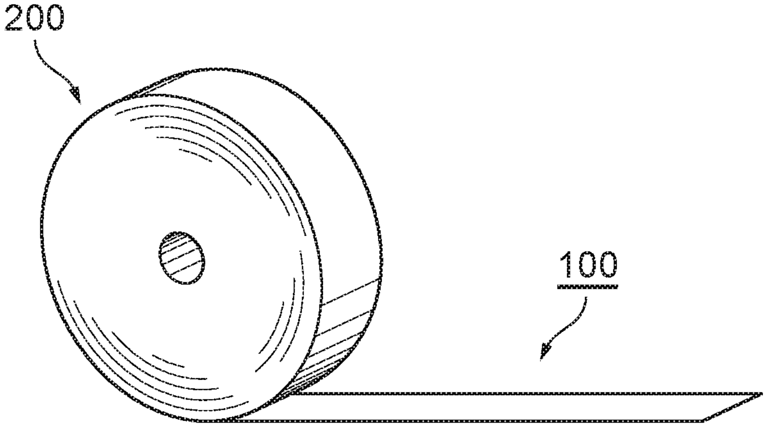
FIG. 3A is a perspective view illustrating a roll product formed by winding the connecting sheet into a roll shape.
Figure 3B:
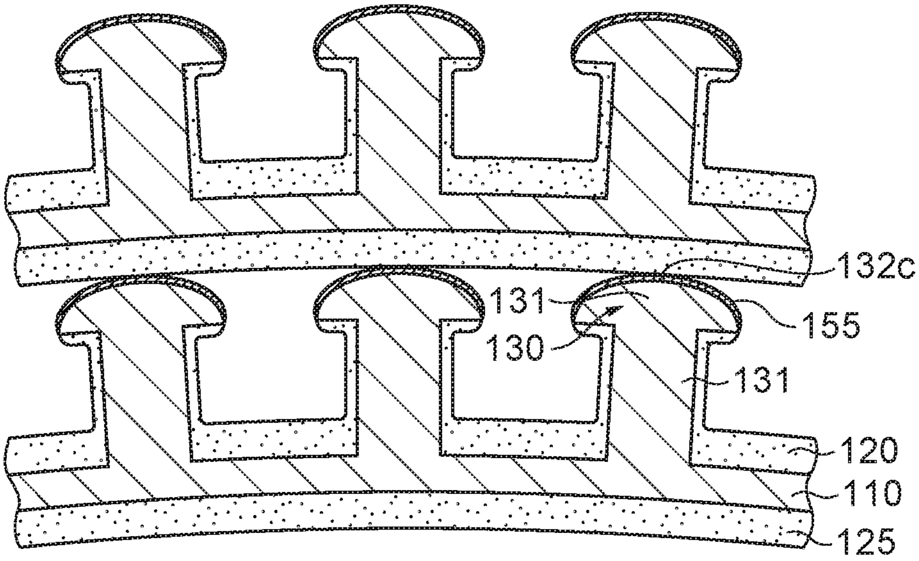
FIG. 3B is a cross-sectional view illustrating the stacked state of the connecting sheet in the roll product.

A release material 155 is applied to an upper surface 132*c* of the head portion 132 of the hook component 130. As a result, the adhesive material is not applied to the upper surface 132*c* of the head portion 132. Here, as illustrated in FIG. 3A, the connecting sheet 100 may be wound into a roll shape to be distributed as a roll product 200. At this time, as illustrated in FIG. 3*b*, the connecting sheet 100 is wound into a roll shape such that the first main surface 110*a* is disposed on the outer circumferential side. The hook components 130 are disposed so as to protrude from the first main surface 110*a* toward the outer circumferential side. Accordingly, the second adhesive layer 125 on the side of second main surface 110*b* is stacked on the upper surfaces 132*c* of the head portions 132 of the hook components 130 disposed on the inner circumferential side. Because the release material 155 is applied to the upper surface 132*c* of the head portion 132 and no adhesive is disposed on the upper surface, the stacked second adhesive layer 125 can be quickly peeled from the upper surface 132*c*.

Next, actions and effects of the connecting sheet 100 in accordance with the present embodiment will be described.

The connecting sheet 100 is the connecting sheet 100 stacked on the object 150 to be connected to the object 150, and includes: a sheet substrate 110 having a first main surface 110*a* and a second main surface 110*b*; a first adhesive layer 120 formed on the first main surface 110*a* of the sheet substrate 110; and a plurality of hook components 130 that protrude from the first main surface 110*a* of the sheet substrate 110 in the Z-axis direction and are spaced at intervals in the XY axial direction in which the first main surface 110*a* extends, and the hook components 130 each includes: a column portion 131 that extends from the sheet substrate 110 in the Z-axis direction and protrudes from the surface of the first adhesive layer 120, and a head portion 132 that extends from the tip of the column portion 131 in the XY axial direction, and the lower surface 132*a* of the head portion 132 is covered with the adhesive material.

Figure 4:
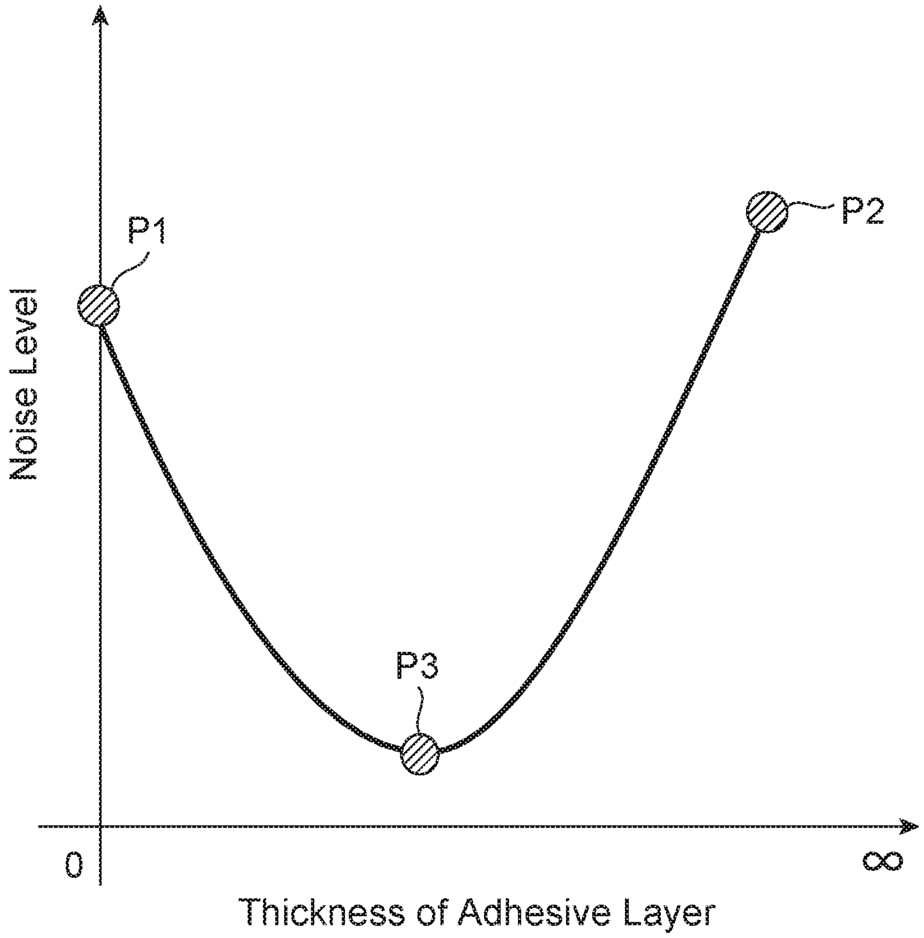
FIG. 4 is a graph illustrating the relation between the thickness of a first adhesive layer of the connecting sheet and noise level.

FIG. 4 is a graph illustrating the relation between the thickness of the first adhesive layer 120 of the connecting sheet and noise level. The noise level indicates the magnitude of noise generated when the connecting sheet is peeled from the object. A measurement point P1 indicates a measurement result in the state where the thickness of the first adhesive layer 120 is 0, that is, when the first adhesive layer 120 is not formed. A measurement point P2 indicates a measurement result in the state where the thickness of the first adhesive layer 120 is large and the hook components 130 are completely buried in the first adhesive layer 120. In other words, the measurement point P2 indicates the noise level in the connecting sheet constituted only of the adhesive layer. As illustrated in FIG. 4, the noise level decreases as the thickness of the first adhesive layer 120 is increased from the measurement point P1, decreases as the thickness of the first adhesive layer 120 is decreased from the measurement point P2, and becomes minimum at a measurement point P3. In this way, as in the connecting sheet 100 in accordance with the present embodiment, when both the hook components 130 and the first adhesive layer 120 are connected to the object, noise generated at peeling can be reduced.

In this manner, the effect of reducing noise at peeling of the connecting sheet 100 is obtained by a combination of a plurality of factors. For example, when both the hook components 130 and the first adhesive layer 120 are connected to the object 150, the first adhesive layer 120 is intermittently bonded to the object 150. In this case, noise at peeling can be reduced as compared to the peeling from the state where the first adhesive layer 120 is wholly bonded to the surface of the object 150. In addition, the lower surface 132*a* of the head portion 132 of the hook component 130 is covered with the adhesive material. Accordingly, when the head portion 132 of the hook component 130 disengages from the fiber or the like of the object 150 at peeling, the adhesive material functions as a cushion. As a result, the force of deformation at peeling of the head portion 132 attenuates, reducing generated noise.

Further, the adhesive strength of the first adhesive layer 120 is 2 (N/25 mm) to 14 (N/25 mm). In this case, noise generated at peeling can be suppressed while securing the coupling force between the connecting sheet 100 and the object 150.

The height of the hook components 130 from the first main surface 110*a* is in the range of 170 μm to 330 μm. In this case, noise generated at peeling can be suppressed while securing the coupling force between the connecting sheet 100 and the object 150.

The connecting sheet 100 further includes the second adhesive layer 125 formed on the second main surface 110*b* of the sheet substrate 110. In this case, the connecting sheet 100 is fixed to another member via the second adhesive layer 125.

The release material 155 is applied to an upper surface 132*c* of the head portion 132 of the hook component 130. This prevents the adhesive material from being applied to the upper surface 132*c* of the head portion 132.

The connecting sheet 100 is wound into a roll shape such that the first main surface 110*a* is disposed on the outer circumferential side. In this case, the connecting sheet 100 can be unwound from the roll to cut a required amount of the connecting sheet 100.

The napkin 1 is provided with the aforementioned connecting sheet 100 on the connecting surface connected to the garment. In this case, noise generated when peeling the napkin 1 from the garment can be reduced.

Also, common napkins are packaged individually. A packing material is nonwoven fabric, film, paper, or the like. In conventional napkins, the connecting sheet is constituted of only an adhesive material layer and thus, the adhesive material when exposed adheres to the packing material, resulting in a failure to peel or damage. Thus, conventionally, a release liner has been covered on the adhesive material layer, or a release material has been applied to the packing material. On the contrary, in the napkin 1 including the connecting sheet 100 in accordance with the present embodiment, the adhesive strength to the packing material can be suppressed, advantageously eliminating the release liner and application of a release layer to the packing material. Further, a misalignment with the packing material can be prevented by the hook components 130, advantageously preventing wrinkles and the like on the napkin 1 due to the movement of the napkin 1 in the packing material.

The present invention is not intended to be limited to the embodiments described above.

For example, the shape of the hook components is not limited to the embodiment described above, and may be any shape. In other words, as long as the hook component has the column portion and the head portion and the adhesive material layer can be formed on the lower surface of the head portion, the shape of the hook component is not particularly limited.

Examples will be described below, but the present invention is not intended to be limited to the examples described below.

EXAMPLES

Figure 5A:
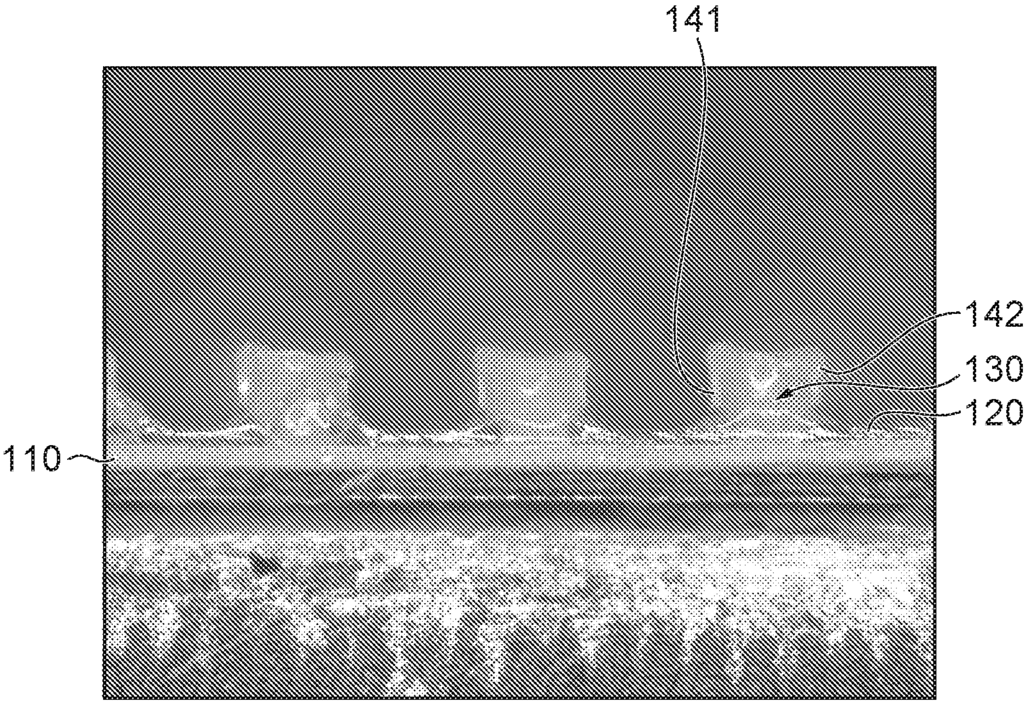
FIG. 5A is an enlarged photograph of the connecting sheet in Example.
Figure 5B:
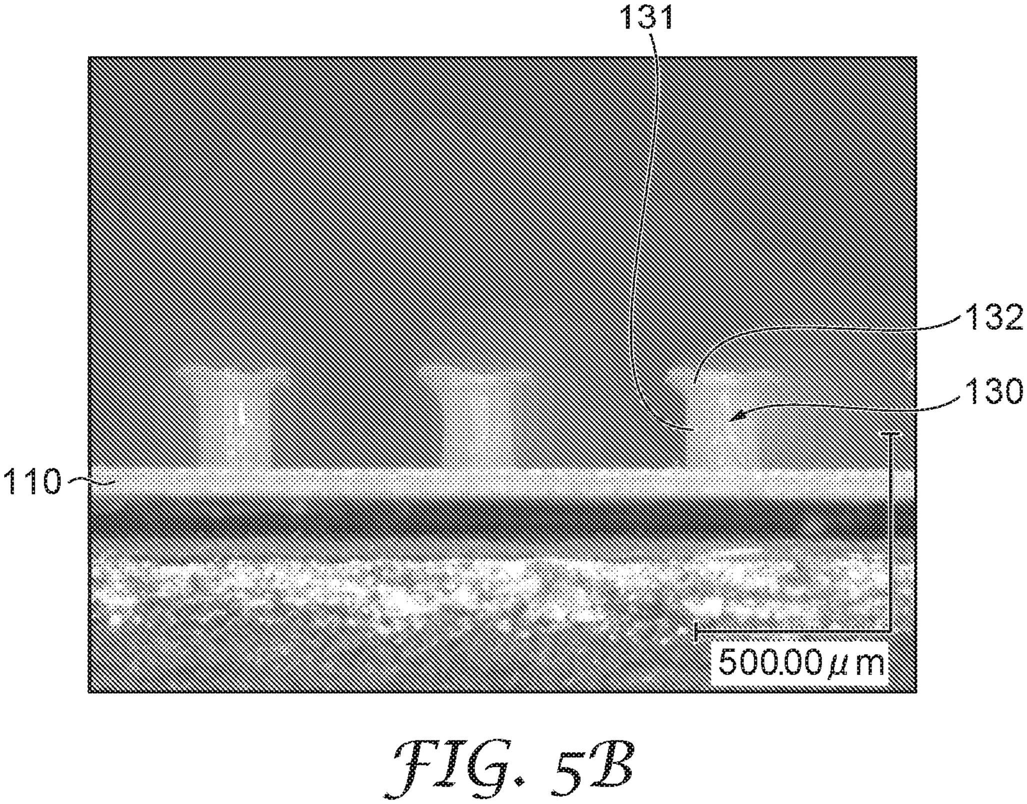
FIG. 5B is an enlarged photograph illustrating the connecting sheet prior to application of an adhesive material.

In Example 1, the first adhesive layer 120 and the adhesive material applied portions 141, 142 as illustrated in FIG. 5A were formed on the sheet substrate 110 having the hook components 130 as illustrated in FIG. 5B. At this time, the height of the hook components, the configuration of the adhesive material configuration, the amount of application of the adhesive material, the adhesive strength, and the shear force were set as illustrated in FIG. 6. The adhesive strength was measured by applying 80 μm of adhesive material to a PP film, sticking the PP film to an SUS panel, and performing 90° peel at 300 (mm/min) according to JIS Z 0237. The adhesive strength is indicated in units of "N/25 mm". The shear force was measured by sticking it to cotton bonded to a metal panel and pulling at 300 (mm/min) in the shear direction. The units of shear force are indicated as "N/20 mm×25 mm". In addition, the diameter of the column portion of the hook component was 250 μm, the diameter of the head portion was 290 μm, and the thickness of the head portion was 80 μm. The density of the hook components was, 1600 pins/square inch.

In Example 1, different amounts of application of the first adhesive layer made of different adhesive material was used to prepare Example 2 (see FIG. 7) and Example 3 (see FIG. 8). In Example 1, the first adhesive layer was eliminated to prepare Comparative Example 1, and the hook components were eliminated to prepare Comparative Example 2 (see FIG. 6). In Example 2, the hook components were eliminated to prepare Comparative Example 3 (see FIG. 7). In Example 3, the hook components were eliminated to prepare Comparative example 4 (see FIG. 8). In Example 1, the height of the hook components and the adhesive material were changed to prepare Examples 4, 5 (see FIG. 9). A commercial product having no hook component ("Sofi Hadaomoi (registered trademark) soft type 25 cm" available from Unicharm Corporation) (assumed to use hot melt as an adhesive layer) was used as Comparative Example 5 (see FIG. 9).

For Examples 1 to 5 and Comparative Examples 1 to 5 described above, the magnitude of noise generated at peeling was measured. In the measurement, the connecting sheets in Examples 1 to 5 and Comparative Examples 1 to 5 were fixed to a napkin, and the napkin was connected to underwear via the underwear via each of the connecting sheets. Then, noise generated when the napkin was peeled from the underwear by hand was measured. The noise measurement was performed using a precision noise meter device manufactured by Lion Corporation. In the measurement, the magnitude (dB) of noise at each frequency of 31.5 to 8000 Hz was measured. FIG. 6 to FIG. 9 illustrate measurement results.

The frequencies of noise recognized as noise by the user is in the range of 500 to 4000 Hz. In FIG. 6 to FIG. 8, the results of Examples 1 to 3 at the frequencies are hatched. At the frequencies, FIG. 6 demonstrates that noise of Example 1 is smaller than noise in Comparative Example 1 and Comparative Example 2, and the relation as illustrated in the graph in FIG. 4 holds. Similarly, in Example 2 in FIG. 7 and Example 3 in FIG. 8, the relation as illustrated in the graph in FIG. 4 holds.

What is claimed is:

1. A connecting sheet stacked on an object to be connected to the object, the connecting sheet comprising:
- a sheet substrate having a first main surface and a second main surface;
- a first adhesive layer formed on the first main surface of the sheet substrate wherein an adhesive strength of the adhesive on the first adhesive layer and the adhesive-coated area is 2 (N/25 mm) to 8 (N/25 mm); and
- a plurality of hook components protruding in a first direction from the first main surface of the sheet substrate, the hook components being spaced at intervals in a second direction in which the first main surface extends, wherein the hook components each include:
  - a column portion extending from the sheet substrate in the first direction, the column portion protruding from a surface of the first adhesive layer;
  - a head portion extending from a tip of the column portion in the second direction, wherein a lower surface of the head portion is covered with an adhesive material, and wherein an upper surface of the head portion is free of the adhesive material, and wherein a release material is applied to the upper surface of the head portion; and
  - wherein the height of the hook components from the first main surface is between 170 μm and 330 μm.

2. The connecting sheet according to claim 1, further comprising a second adhesive layer formed on the second main surface of the sheet substrate.

3. The connecting sheet according to claim 1, wound into a roll shape such that the first main surface is disposed on an outer circumferential side.

4. A garment sticking article comprising the connecting sheet described in claim 1 on a surface connected to a garment.

5. The garment sticking article of claim 4, wherein the garment comprises underwear.

* * * * *